(12) United States Patent
Weitzel

(10) Patent No.: US 8,885,906 B2
(45) Date of Patent: Nov. 11, 2014

(54) ALIGNMENT OF POSITRON EMISSION TOMOGRAPHS BY VIRTUAL TOMOGRAPHS

(75) Inventor: Thilo Weitzel, Herrenschwanden (CH)

(73) Assignees: Universitat Bern, Bern (CH); Universitatsklinik fur Nuklearmedizin, Bern (CH)

( * ) Notice: Subject to any disclaimer, the term of this patent is extended or adjusted under 35 U.S.C. 154(b) by 211 days.

(21) Appl. No.: 13/639,618

(22) PCT Filed: Apr. 7, 2011

(86) PCT No.: PCT/CH2011/000074
§ 371 (c)(1),
(2), (4) Date: Mar. 4, 2013

(87) PCT Pub. No.: WO2011/123964
PCT Pub. Date: Oct. 13, 2011

(65) Prior Publication Data
US 2013/0202172 A1    Aug. 8, 2013

(30) Foreign Application Priority Data

Apr. 8, 2010 (CH) ......................................... 505/10

(51) Int. Cl.
| | | |
|---|---|---|
| *G06K 9/00* | (2006.01) | |
| *G06T 7/00* | (2006.01) | |
| *G06T 5/00* | (2006.01) | |
| *G06T 11/00* | (2006.01) | |

(52) U.S. Cl.
CPC ...... *G06T 7/0012* (2013.01); *G06T 2207/10081* (2013.01); *G06T 5/003* (2013.01); *G06T 2207/10104* (2013.01); *G06T 11/008* (2013.01)
USPC ........................................................ 382/131

(58) Field of Classification Search
None
See application file for complete search history.

(56) References Cited

U.S. PATENT DOCUMENTS

| | | | | |
|---|---|---|---|---|
| 2008/0037846 | A1* | 2/2008 | Avinash et al. | 382/131 |
| 2010/0067766 | A1* | 3/2010 | Vija | 382/131 |
| 2010/0245602 | A1* | 9/2010 | Webster et al. | 348/208.4 |
| 2011/0169943 | A1* | 7/2011 | Bachman et al. | 348/117 |
| 2013/0101194 | A1* | 4/2013 | Zeng | 382/131 |

OTHER PUBLICATIONS

Olivier Rousset et al. "Partial Volume Correction Strategies in PET" PET Clinics, WB Saunders Co, US, vol. 2. No. 2, Apr. 1, 2007, pp. 235-249, XP002525044, ISSN: 1556-8598, DOI: DOI:10.1016/J.CPET.2007 10.005.

* cited by examiner

*Primary Examiner* — Hadi Akhavannik
(74) *Attorney, Agent, or Firm* — Dilworth & Barrese, LLP.

(57) ABSTRACT

Positron emission tomography, possibly in combination with computed tomography, allows in addition to medical diagnostic imaging the quantitative determination of various parameters. Quantitative measurements using tomographs exhibit a severe and unavoidable dependency on the imaging properties of the respective tomograph, which makes quantitative assessment of the results difficult. This relates particularly to multicentric medical studies, which obligatorily require quantitative comparability of the data measured by the participating centers. The methods claimed herein include the definition of a virtual tomograph with defined imaging properties. The claimed methods also cover determination of the imaging properties of different tomographs on the basis of suitable reference measurements and possibly by using a calibration phantom. Based on the definition of the virtual tomograph and the determination of the imaging properties of different tomographs, the methods according to the invention then allow conversion and subsequently standardized and quantitatively comparable representation of the image data recorded by the different tomographs or systems as if all measurements were acquired equally by the virtual system. The method according to the invention therefore supports the quantitative evaluation of image data in multicentric studies.

18 Claims, No Drawings

ALIGNMENT OF POSITRON EMISSION TOMOGRAPHS BY VIRTUAL TOMOGRAPHS

BACKGROUND OF THE INVENTION

Positron emission tomography (PET), optionally in combination with computed tomography (PET/CT), allows besides medical diagnostic imaging the quantitative determination of various parameters. Preconditions for such quantitative measurements on patients are the strict adherence to standardized clinical protocols, as well as an absolute calibration or cross calibration of the tomographs used.

The requirements for uniform clinical protocols as well as the requirements for cross calibration of the tomographs and for methods to determine quantitative values currently are intensively discussed particularly in the context of multi-centre medical studies [WAHL09], [BOEL09], [BOEL09b], [DELB06], [SHYA08] [SCHE09].

Quantitative measurements acquired by tomographs, however, show a strong and unavoidable dependence on the imaging properties of the particular tomograph, notably on the spatial transfer function (Point Spread Function, PSF), which differs from each other tomograph. Due to the different transfer functions, any quantitative assessment is made difficult even for otherwise calibrated tomographs or other certified medical imaging device. This applies particularly to multi-center medical studies which demand a quantitative comparison of the measured data of the participating centers.

In positron emission tomography the most commonly used quantitative measure for the activity measured in a tissue is the "standardized uptake value" (SUV) in different variants [BOEL09]. It has been shown that determination of an SUV can be performed with great repeatability when a strictly defined examination protocol is adhered to and the same tomograph is used in each measurement.

It is these measurements, however, which possibly show very different results, if different tomographs are used, even if the devices are calibrated. The differences mainly are due to the partial volume effect (PVE), which causes the activity of small objects to be systematically underestimated. This effect is closely related to the spatial transfer function of the particular tomograph.

Aside from the spatial resolution determined by the half width of the transfer function the exact shape of the transfer function is of particular interest. Thus, even when having same spatial resolution, different tomographs may show very different partial volume effects (PVE). Various methods to minimize the impact of PVE on quantitative measurements, especially SUV measurements, have been proposed [KEYE95] [STRA91] [BOEL03] [WEST06] [SORE07].

Using these often complex methods and if need be employing independent measurements for the determination of the volume of an object, it is possible to increase the accuracy of the measurements or to extend the available measuring range to towards smaller objects. Nevertheless the results still depend on the tomograph used.

Therefore, in the context of multi-centre studies, the benefits of those methods are very limited.

In quantitative PET studies and particularly in studies, which need to be carried out repeatedly over a long period of time or at different sites, a standardized tomograph would be required, which could provide reproducible measurements anywhere at any time.

Unfortunately, such a standardized PET system is not available, on the one hand due to the large number of available systems of different manufacturers, on the other hand as a result of continuous technical development of the systems and the resultant constant changes of devices.

SUMMARY OF THE INVENTION

The essential aspect of quantitative measurements is the ability to compare measurements with each other.

In the context of PET a measurement of a SUV can be carried out as a base for therapy control (comparison of multiple measurements over time), as a base for classification (comparison of measurements on a plurality of patients), or in the context of a medical study (follow-up, or classification with a large number of patients from different groups) as a criterion, for example for the efficacy of a drug.

Thus in practice, the repeatability and especially the comparability of measurements is of much higher importance than an accurate absolute quantification, even if different tomographs are used.

Comparability requires de facto a standardization of tomographs, and in particular requires a uniform PSF for all tomographs. For obvious reasons such a standardized tomograph is not available in reality.

DESCRIPTION OF THE PREFERRED EMBODIMENTS

Origin of the invention is the development of a process, which, following a precise metrological characterization of a particular tomograph by means of determining its respective spatial transfer function, allows to convert data measured by this first tomograph in such a way that the resulting data looks like if it was measured by a second, different tomograph with known transfer function.

Within certain constraints this method allows for the definition of a virtual tomograph in such a way, that it becomes possible to convert image data sets acquired by different real tomographs as if they had each been recorded by the defined virtual tomograph. Following this conversion all data sets, originally recorded by different real tomographs, become now directly usable for quantitative comparison.

The methods claimed herein include the definition of a standardized virtual tomograph or a standardized virtual imaging system with a known and fixed transfer function as a base for the cross calibration of different positron emission tomographs or other medical imaging systems.

The claimed methods further comprise a determination of the imaging characteristics of different tomographs or imaging systems starting from suitable reference measurements and when indicated using a calibration phantom. In addition to preferred technical designs for such a calibration phantom, the claims also describe constraints that should be met in the measurements, particularly concerning the linearity of the respective measurements.

Starting from the definition of the standardized virtual tomograph and the determination of the imaging properties of different real tomographs the methods of the invention then allow a conversion and subsequently a uniform and quantitatively comparable representation of data measured by the different tomograph or systems. This comparable representation of imaging data takes place in such a way, as if all measurements had been likewise carried out by the standardized virtual system.

Transconvolution

The claimed method for handling a virtual tomograph envisages, inter alia, the use of several numerical mathematical operations, in particular a combination of convolution and deconvolution, which is referred to hereinafter as Transconvolution.

As part of the claimed method at first a standardized virtual tomograph or a virtual imaging system is defined by specifying a suitable point spread function (PSF), and the real tomographs, respectively imaging systems, are characterized by appropriate measurement of their respective PSFs.

The numerical process called transconvolution can be represented as a convolution of the measured images with the inverse of the PSF of the correspondent acquiring tomograph (deconvolution) followed by a convolution of the result with the defined transfer function of the virtual tomograph. This process can be represented as follows:

$$img \otimes psf^{-1} \otimes F^{-1}(H) = img_n$$

wherein img stands for the image acquired by the respective tomograph with its respective transfer function psf, and $F^{-1}(H)$ stands for the defined PSF of the standardized virtual tomograph.

The latter is represented herein as a Fourier transform of an aposidation function H.

In each case, the result is a standardized image $img_n$ that may serve as a starting point for standardized and comparable quantitative analyses.

By defining the virtual tomograph or respectively a virtual imaging system as a standard, the process pursuant according to the invention can thus effectively support the quantitative evaluation of image data in multi-centre studies.

To determine the respective PSFs of the different tomographs, reference measurements, using a dedicated solid body phantom, are proposed.

For handling of the claimed method in the context of medical imaging systems, particularly positron emission tomography, the reconstruction and joint management of two different image data sets is proposed, while leaving the original recoding process untouched. One data set results from reconstruction for optimal visualization of the images; a second data set results from an as linear as possible reconstruction for the quantitative measurements. This second data set can then, based on the known PSF, be recalculated with the aid of numerical Transconvolution in a manner, such as if acquisition had been carried out by the standardized virtual system. Based on such a standardized data set, quantitative measurements are thus normalized and comparable with correspondent other normalized measurements.

The main purpose of the method is to improve the validity of clinical trials and in particular to support and improve multi-centre clinical trials.

In addition to an application in the field of positron emission tomography, the method can also be applied to other complex imaging techniques, for instance different tomographs, ultrasound imaging or other scanning methods such as confocal microscopy.

Relevant Aspects of Imaging and Image Processing

Based on the physical properties of light, in particular the propagation of light in the form of an electromagnetic wave, numerical methods in Fourier space and its use in imaging are very well understood. Resultant methods such as Wiener deconvolution or iterative deconvolution with the help of statistical criteria have been established in various areas of imaging or spectroscopy. The importance of stationary or non-stationary PSFs and physical limits of resolution or image quality as a result of stationary or non-stationary photon noise is precisely defined [ERSO07], [GOOD96].

Accordingly, the effects of discrete sampling in spatial, spectral, and temporal coordinates and the digital representation of intensities are in turn incorporated in the mathematical models [BENE01]. Furthermore, the performance of today's computers permits the routine use of numerical methods in Fourier space also for large three dimensional data sets, particularly in the area of medical imaging.

Nevertheless, it must be cautioned that these numerical methods, which were originally developed in the field of Fourier optics, are directly based on fundamental physical properties of light in the context of optical imaging devices. For this purpose and within the limits imposed by Poisson statistics of photon noise strictly linear superposition plays an important role.

For non-optical medical imaging equipment and especially for tomograph these basic characteristics are not primarily met. The use of Fourier methods in medical imaging can possibly exaggerate linear effects and can thus complicate quantitative assessment.

Fundamentals of PET and PET/CT Imaging

PET/CT imaging is carried out both for the PET as well as for the CT in three clearly separate steps: data acquisition, sinogram calculation and reconstruction of the images. Each step has its own specific characteristics and parameters and contributes to overall system performance. Moreover, the CT is critical for attenuation correction of the PET acquisition itself and constitutes for this reason an integral part of image quantification.

The technical details of contemporary clinical devices are being discussed to great extend [TARA03] [CHER06] [TOWN08].

The following sections focus on the linearity of the aforementioned steps as the basis of quantitative measurements.

PET Data Acquisition

Clinical PET/CT systems continue to benefit from the ongoing technical development. Better and faster scintillators, photo detectors, electronics and computers allowed the transition from 2D detection of coincident signals to a full 3D acquisition and progressed now to "time-of-flight" (TOF) sensing.

Nevertheless, the basic principle of the coincidence measurement has not changed and within the limits of photon and background noise the acquisition process remains linear. Although some parameter of the measurement process can vary over the field of view and over the measurement volume, the exact characteristics of the data collection as a whole, starting from a fixed structure and stable parameters of scintillators and detectors are very well defined. Therefore, and basing on the measurement principle, it can be assumed that the PET data acquisition is linear over a wide range.

Calculation of the PET Sinogram

Every during data acquisition registered coincidence event is interpreted as an intensity distribution along a "line of response" (LOR) or a "tube of response" (TOR), connecting the involved scintillators. Each LOR or TOR can be represented numerically by an angle and an offset from the centre of the field of view. Starting from values for angles and offsets used as coordinates, the sinogram is then generated by numerically projecting the coincidence events onto a two or three dimensional coordinate system; i.e. creating a correspondent data volume.

The process can be used simultaneously to carry out an attenuation correction by increasing the relative weighting of LORs in accordance with a previously calculated attenuation mask and thus compensating for the encountered signal attenuation.

Furthermore, the TOR concept allows for the incorporation of certain corrections, where the TOR diameter is varied to include, for example, characteristics of geometrical detectors arrangements or different detection sensitivities [HERR07]. Likewise, time of flight information (TOF) can be integrated in order to limit the relative contribution of an event to only a partition along the LOR or TOR.

In any case, during or after the projection interpolation and re-sampling has to take place. As such, the resultant data set is provided independently of the precise geometric arrangement of the detectors and in a form suitable for the following numerical method. A suitable and commonly used technique is "Fourier rebinning" (FORE).

The sinogram creation including both attenuation correction as well as the consideration of TOF information, the geometric characteristics of the scintillators and the respective Fourier rebinning can be considered, within the limitations set by noise, as linear processes. These various corrections may lead to deviations both from the expected Poisson statistics of the noise as well as from an inhomogeneous noise distribution in relation to the field of view of the tomograph.

Apart from the aforementioned effects onto the properties of the noise component, it is possible for this "primary" sinogram to define, while not a stationary, but a linear PSF. On the basis of such a PSF quantitative measurements are thus possible.

In a next step, numerical methods ("sinogram restoration methods") are used to increase the sinogram resolution by inverse filtering. For instance, the application of a Wiener filter (Wiener deconvolution) can have positive effects on the spatial resolution but increases the amount of noise in return. This leads to a further distortion of the statistical properties of the noise component [HERR06].

Advanced numerical methods applied onto the sinogram, such as iterative deconvolution ("maximum likelihood deconvolution") and the use of non-stationary PSFs, can further improve the resolution of the sinogram but depend inter alia on the particular local noise component and the present data itself. These methods may thus have strong non-linear effects and should therefore be avoided in the context of quantitative measurements.

PET Image Reconstruction

Based on the sinogram, the actual image, respectively the from the measurement resultant data volume, is calculated in the third step (reconstruction). Filtered back-projection (FBP) is a for this purpose suitable simple, reliable, fast and above all linear procedure. In imaging a reconstruction using FBP achieves an acceptable spatial resolution based on the half-width (full width at half maximum, FWHM) of the resultant PSF.

However, the PSF shows relatively broad wings, which causes image blur and impedes quantitative measurements. This is especially true, because the wings of the PSF in volume data spreads out in all 3 dimensions and cause for this reason an overflow effect between voxels ("spill-in", "spill out").

In the context of quantitative measurements it has to be emphasized that FBP is principally a linear operation and, starting from a suitable sinogram leads to a stable and reproducible PSF.

Unless already taken place in the sinogram, attenuation correction can be linked to the FBP or be applied directly to the resultant image.

Modern iterative reconstruction methods depending on statistical criteria such as "maximum likelihood expectation maximum" (MLEM) or "ordered subset expectation maximum" (OSEM) have become the standard for reconstruction of PET images. In principle, these methods implement a method which at first allows the inverse calculation of a sinogram starting from an image and known properties of the particular tomograph. The process then iteratively modifies an initially coarse image until the corresponding calculated sinogram shows an as good as possible accordance with the sinogram generated from the actual measurement.

By specifying appropriate boundary conditions, the process is controlled in a way that a good compromise between increased spatial resolution, suppression of the foot of the PSF and the resultant noise is achieved. As a consequence of their statistical nature, the iterative methods are susceptible to variations in the noise component of the original measurement, as well as to properties of the image content itself.

While the iterative methods display a higher spatial resolution compared to FBP and therefore are able to reduce the disturbing influence of the PVE on comparably small objects during quantitative measurements, it remains unclear how far those improvements really go.

Although, with overall improved imaging and accuracy but in the particular case with actually unknown and variable PSF the benefit of iterative methods with respect to the needs of comparability of measurements remains limited. This is particularly true in the context of multi-centre studies.

The Standardized Uptake Value (SUV)

In the context of PET the concept of the SUV describes accumulation of radioactive tracers in tissue depending on injected total dose and weight of the patient. The SUV as a measure is widely used and is intended to provide comparable results. However, the concept shows a remarkable development and variability since its introduction.

The early definitions describe measured activity per gram of tissue and patient's weight in relation to injected activity [OLDE74] [WOOD75]. The original definition of the SUV [STRA91] was defined as the concentration in tissue (mCi/g) per injected dose (mCi/g) per patient body weight (g). The result therefore is a dimensionless, absolute value which can be considered as the ratio between measured activity in a defined volume to an average activity relative to the whole body.

A more current definition in a clinical context can be rewritten as follows:

"The SUV is a measured activity concentration in Bq/ml within a defined volume (volume of interest) with respect to the injected activity in Bq per patient body weight in grams measured at a defined time after injection"

This definition does not lead to a dimensionless value but results in a formal unit g/ml.

Other variants use the body surface of the patient as a reference dimension for normalization [THIE04].

The predominantly used formula for calculating the SUV based on activity concentration within a volume of interest (ACvoi), the injected dose (FDGdose) and body weight (BW) is given by Boellard [BOEL09] as:

$$SUV = \frac{ACvoi[\text{kBq/ml}]}{FDGdose[\text{MBq}]/BW[\text{kg}]} \quad (1)$$

Unfortunately, the definitions suggest no method for the description of the volume of interest (VOI), which allows for implementing the actual measurements in very different versions, resulting in correspondingly different outcomes [BOEL03].

The extremely critical influence of how the measured volume (volume of interest) is defined on the measurement result is well known [KEYE95].

Therefore, by far the most common method of SUV measurement used is to determine the $SUV_{max}$, i.e. the highest value shown by an individual voxel within the VOI is used as a measure of activity.

By simply using this maximum value, the need for a more precise definition of the actual VOI is eluded, and thus the influence of such a manual definition of the VOI or a description of the VOI using a threshold [BOEL09] is avoided. This is despite the obvious disadvantages that occur when a measurement is based on a single voxel.

Measuring $SUV_{max}$

Activity concentration is defined statistically as the mean number of radioactive decays per unit time and volume. The actual measurement of activity concentration therefore is coercively linked to an appropriate definition of the relevant measurement volume. Strictly speaking, it is therefore not possible to specify an activity concentration without also describing the corresponding measurement volume. Furthermore, the definition implies that the measurement is subjected to Poisson statistics, i.e. the measurement accuracy is in any case limited by photon noise (shot noise), or respectively by the number of detected decays within the measuring volume during the measuring time.

The number of detected radioactive decays can be considered as a fraction of the number of true decays, which is reduced by the respective absorption and detection sensitivity.

Differing from the simplified models found in literature, the definition of activity concentration must in each case contain a description of the measurement parameters to refer directly with it to the parameters of the respectively involved PET/CT system.

Based on measurement using a single voxel, a definition must then become something like this:

"The measured activity concentration with respect to a single voxel of a PET image data set represents the number of detected radioactive decays over a, accordingly to the effective tomographs PSF weighted, average of a region centered around the corresponding voxel and corrected for the detection sensitivity of the system and corrected for the, on the measurement situation dependent, attenuation correction."

Thus, a measurement of $SUV_{max}$ is at first inseparable from the spatial transfer function (PSF) of the tomograph that defines the measurement volume. Further, the measurement depends, at least with respect to the statistical accuracy of the measurement, on the sensitivity of the tomograph and the corresponding attenuation.

When spatial variations of the activity concentration in the order of a voxel size occur, the measurement result will be disturbed by the sampling process, as the respective spatial maxima of activity concentration do not necessarily coincide with the respective centers of the voxel itself but rather show a random distribution in relation to their position within the voxel grid.

Partial Volume Effect

The partial volume effect (PVE) (or "spill-in" and "spill out") is the most important factor that limits quantitative PET/CT measurements [SORE07]. The PVE is caused by the limited spatial resolution of the tomograph and is usually characterized as a function of the width at half maximum (Full Width Half Maximum, FWHM) of the PSF.

In practice the PVE concerns all measurements performed on structures with diameters of less than about three times the FWHM. Correspondingly, measurements become generally unreliable, when the activity distribution shows structures with spatial frequencies less than about three times the FWHM.

Source of the PVE is the fact that—as described above—the measurement of activity concentration always represents a weighted average of a region which in turn is given by the PSF. Tails of the PSF range far beyond the FWHM. In 3-dimensional imaging, the effect is exacerbated by the fact that the extensions of the PSF reach out in all 3 dimensions into the surrounding volume and are therefore weighted more by the square of the distance to the centre of each voxel. The diameter of the region which contributes significantly to the signal is thus clearly greater than the FWHM of the PSF. This influence of the surrounding environment on each local measurement distorts the corresponding results, especially when measuring activity concentration off small structures.

Next, the influence of the surrounding environment on the measurement can not be adequately described by the FWHM. Rather, knowledge of the exact shape of the PSF, and especially of the edge regions of the PSF is required. An accurate knowledge of the PSF allows, within certain limits, a PVE correction by deconvolution. Especially is the PVE in principle fully defined by the respectively effective PSF of the measurement.

Clinical PET Protocols for Quantitative Measurements

PET acquisitions for quantitative analysis require strict adherence to study protocols, that specify the preparation of the patient, the preparation and injection of the radiolabel, the technical parameters of the recording itself, the method for reconstructing the images, and of course the methods of numerical analysis of the data for specifying the current measured value. Next, a calibration or cross-calibration of the employed tomograph is required.

Especially in the context of multi-centre medical studies the requirements for uniform testing protocols, for cross-calibration of the tomograph and the methods for determination of quantitative values are being discussed intensively [WAHL09], [BOEL09], [BOEL09b], [DELB06], [SHYA08] [SCHE09].

Although these proposals already contain comprehensive provisions for the necessary research protocols, the measured values are subject to large variations due to different imaging characteristics of the different PET/CT systems available in the respective institutions [WEST2006].

The problem is exacerbated by the fact that the systems have a growing number of variable technical parameters that can be used to optimize the imaging for specific applications, but at the same time hinder a quantitative evaluation of the so-manipulated images.

To improve this situation, the methods claimed herein are aimed at compensating for differences in the imaging properties of the respective imaging systems.

It is proposed in the context of quantitative measurements to prospectively carry out two reconstructions for every PET acquisition and afterwards to handle the resulting image pairs in parallel.

A first reconstruction is performed for optimal imaging using iterative numerical methods for increased spatial resolution and contrast, as required for clinical routine. For quantitative measurements a second reconstruction is carried out in parallel, which is limited to the substantially linear methods.

This second reconstruction—hereinafter referred to as linear reconstruction—is suitable as the starting point for quantitative measurements using the presently claimed methods, since the restriction to a linear reconstruction can ensure a stable transfer function of the system.

Cross Calibration Using Recovery Factors.

The absolute calibration of PET systems based on the measurement of activity concentration is a challenging task [GEWO02].

Based on large homogeneous sources, such as a commercially available doped 68Ge cylinder phantom (20 cm diameter), a mutual adjustment of different PET systems is nevertheless relatively easy to perform [SCHE09]. This is in fact possible because the diameter of the homogeneous phantom exceeds the diameter of the PET systems PSF by far.

For smaller objects this type of calibration will not work anymore. The measurements are affected by the PVE, which varies considerably as a function of both the FWHM of the PSF and of the exact shape of the PSF. Since the PSFs differ significantly between different tomographs and the PVE cannot be corrected without additional information, a simple comparison of different PET systems is not possible.

A recent approach to overcome this problem is the measurement of recovery factors by means of phantom measurements on spheres with homogeneous activity concentration but of different sizes. For every tomograph the measured fraction (=recovery factor) is determined of the actual activity concentration which still can be measured in the centre of a particular sphere. In other words, the PVE for homogeneous spheres of known size in a homogeneous environment is determined by measurement.

In later measurements it is then possible to infer to the actual activity concentration, under the assumptions that the object to be measured is approximately spherical, that it represents a homogeneous concentration of activity in a homogeneous environment, and the its diameter elsewhere—for example in the CT image—can be determined with the help of the respective appropriate recovery factors, [SHYA08].

This method is of course subject to the limitation that the results are accurate only for spherical and homogeneous objects, further to the limitation that the exact size of the sphere must be determined otherwise. Furthermore, for different tomographs with different PSFs inaccuracies will eventually develop in completely different ways; rendering it highly difficult to compare the results for different tomographs.

The methods claimed herein are therefore primarily aimed not at an undetermined absolute correction of the PVE but directly at a comparison of results from different tomographs. Basis of the claimed method is therefore not the determination of recovery factors but, if necessary by using an appropriate phantom—the determination of the actual PSF of the different imaging systems.

Solid State Phantom

Calibration measurements using a phantom or other radiation sources are a foundation of quality assurance for PET systems [DAUB02]. Usually, corresponding "recovery factors" are determined as described above by using different sized spheres with homogeneous activity concentration. Although occasionally additional measurements are made with point sources to measure the FWHM, the particular shape of the PSF is typically not measured or determined more precisely.

To determine the PSF, notwithstanding the otherwise obvious use of a point source, it is herein proposed to use a novel solid-state phantom. This phantom differs from the currently available standard phantoms with active spheres approximately according to the NEMA/IEC 2001 standard in three basic points:

- It is a solid state phantom that is easy to transport, and its spheres need not to be refilled between measurements.
- Compared with the standard phantom this phantom contains more spheres, which together cover a larger range of diameters.
- And the spheres can also be handled individually in many different configurations, allowing a fast realization of phantoms adapt at the respective application, such as a positioning in the vicinity of absorbers or in cavities, or both.

The use of a solid-state phantoms based on the relatively long-lived $^{68}$Ge isotope avoids the otherwise necessary repeated filling of the spheres, and simplifies handling of the spheres significantly. Thus, a number of possible errors are avoided, and in particular the radiation exposure of the persons entrusted with the handling of the phantom is reduces significantly.

Furthermore, the handling of a solid state phantom is, with respect to a phantom filled with activity in liquid form, altogether significantly simplified. This is true independently of the number of containing spheres. On this basis, and to allow a more accurate determination of the PSF and owing to the higher spatial resolution of modern PET/CT systems, the number of spheres was extended to smaller diameters.

The for the evaluation of the claimed methods prepared Phantom uses twelve hollow spheres which comprise volumes of 16 ml down to $^{1}/_{128}$ ml, corresponding to diameters of approximately 31 mm down to 2.5 mm. The spheres were filled homogeneously with an epoxy resin mixed with an activity concentration of 0.1 MBq/ml. After the resin has cured and additional sealing of the openings for the filling of the balls, they can be handled in a simple manner without the risk of contamination.

The spheres were mounted inside a Plexiglas cylinder of 22 cm in diameter on two concentric circles. On the outer circle with about 14 cm in diameter the 6 larger balls are mounted; the inner circle with about seven cm in diameter mounts the six smaller spheres. The Plexiglas cylinder can be filled with water.

Moreover, the individual spheres are designed such, and with an appropriate thread for attachment provided, that they can be used in the simplest way within other arrangements. In particularly in the context of specific medical problems, it is easily possible to setup an arrangement which, with reference to radiological characteristics, simulates certain anatomical features.

For instance, in the context of medical studies using PET/CT images, the accuracy of cross calibration of different devices in context of a certain problem can be increased by means of phantoms adapted to that particular problem.

Determination of the Point Spread Function

The process of imaging that yields the image (img) is typically illustrated as a convolution of a object representing preimage (obj) together with a device specific PSF (psf):

$$\text{obj} \otimes \text{psf} = \text{img} \qquad (2)$$

Obviously, the PSF can therefore be defined as the image of a point source (point) in the centre of the coordinate system:

$$\text{point} \otimes \text{psf} = \text{psf} \qquad (3)$$

Usually, the PSF of an imaging system or of a tomograph is measured with the help of an image formed by a point source, i.e. by using a source of a diameter much smaller than the FWHM of the PSF to be surveyed. In fact, this method is not always optimal, since the image of a point source is generally not the found in actual applications of such a system.

Typically, objects are mapped with structures of finite size, and it seems plausible, to also determine the PSF by using objects with a size similar to the usually imaged objects of interest. For determining the PSF of a PET system, therefore, a measurement on the above described phantom, i.e. measurements on homogeneous spheres of known size, are suggested starting directly from equation (2).

For the case of a well known object, and thus a well-known preimage (obj) and, together with the available measured image (img), it is possible to determine the PSF by numerical deconvolution, i.e. by convolving the image (img) with the inverse Fourier-transform of the object (obj$^{-1}$) accordingly to the subsequent equation:

$$\text{psf} = \text{img} \otimes \text{obj}^{-1} \qquad (4)$$

In practice, a numerical determination of the PSF by iterative numerical deconvolution methods is readily possible on the grounds of equation 2.

This method is apparently more robust than the usual method using a point source, because a larger number of voxels contributes to the result, and because the output measurements performed on several differently sized spheres come close to the context of the actual desired clinical measurements.

Starting from a single measurement of the previously described phantom, it is therefore possible to obtain both the actual PSF, as well as an absolute measure for cross-calibration of different PET systems. Furthermore, a measure of the sensitivity results, for example in the form of a detectable signal to noise ratio related to the measurement situations that can be represented by the phantom.

It should be noted that the PSF of a PET system is in general not stationary, and, with increasing trans-axial distance from the centre of the field of view, is subject to systematic broadening. Depending on the requirements, this spatial variation of the PSF must be considered accordingly. This can be done with the help of several measurements of the phantom at different positions in the tomographs field of view, and the calculation and presentation of a position-dependent PSF by suitable interpolation or extrapolation of the, at each of the different locations of the measurement determined, local PSFs, or with the help of a mathematical transformation of the measured local PSF according to known technical characteristics of the tomograph.

Transconvolution

As shown above, the measurement of SUV is inseparably related to characteristics of the tomograph. In particular, the determination of SUV$_{max}$ is directly related to the PSF of the respective tomograph.

Strictly speaking, an absolute determination of the SUV, at least for small objects, is not only impossible but not even definable, because activity concentration measurement implies in any case a given measurement volume. As previously described the measurement volume is defined by the PSF of the respective tomograph.

In order to obtain valid and comparable values from SUV measurements a standardization of the PSF of the used tomographs would be mandatory or the use of a standard tomograph for all measurements respectively. Unfortunately, for obvious reasons, the competing manufacturers of PET/CT systems are not interested in the production of standardized tomographs with identical properties from all manufacturers.

To overcome this problem, a new numerical method is proposed that in the following is referred to as Transconvolution.

To explain the method initially two different imaging systems are defined as follows:

$$\text{obj} \otimes \text{psf}_1 = \text{img}_1 \qquad (5a)$$

$$\text{obj} \otimes \text{psf}_2 = \text{img}_2 \qquad (5b)$$

The two different point spread functions $\text{psf}_1$ and $\text{psf}_2$ represent the two different tomographs or different imaging systems, which accordingly generate the two different images $\text{img}_1$ and $\text{img}_2$ of the same object obj.

In theory with known PSF the object could be reconstructed mathematically by means of deconvolution, i.e. by an inverse filtering formed as follows:

$$\text{img}_1 \otimes \text{psf}_1^{-1} = \text{obj} \qquad (6)$$

For real-world measurements with a limited number of data points (sampling), limited resolution, and in the presence of noise, the scope of such a deconvolution is very limited. Specifically, the inverse of the point spread function ($\text{psf}_1^{-1}$) can typically not be represented numerically.

However, from equations (5) and (6) follows:

$$\text{img}_1 \otimes \text{psf}_1^{-1} \otimes \text{psf}_2 = \text{img}_2 \qquad (7)$$

This formula describes how, with known point spread functions of the respective imaging systems ($\text{psf}_1$, $\text{psf}_2$), the image of an object, as it is created by a first imaging system ($\text{img}_1$), can be transformed in such a way that a second image is formed ($\text{img}_2$) corresponding to the image of the object, as if it was created by a second different imaging system.

For further explanation the Transconvolution function (tf) is introduced as follows:

$$\text{tf} = \text{psf}_1^{-1} \otimes \text{psf}_2 \qquad (8)$$

$$\text{img}_1 \otimes \text{tf} = \text{img}_2 \qquad (9)$$

In general, the inverse of a PSF cannot be represented numerically, so that $\text{psf}_1^{-1}$ cannot be fully defined. The convolutions described by equations (8) and (9), however, can be described a simple manner following Fourier transformation in frequency space in as follows:

$$F(\text{tf}) = F(\text{psf}_1^{-1}) \cdot F(\text{psf}_2) \qquad (10)$$

$$F(\text{img}_1) \cdot F(\text{tf}) = F(\text{img}_2) \qquad (11)$$

Based on a point spread function psf the term |F(psf)| is defined as the corresponding modulation transfer function (MTF) of the system with respect to the transmitted spatial frequencies. For any realistic imaging system the MTF will slope down for higher spatial frequencies and above a certain cut-off frequency eventually will drop below any in each case present noise level.

The inverse of a point spread function can obviously only be determined meaningfully for values below this cut-off frequency.

This fact is the underlying reason for the fundamental limitations of deconvolution.

The mathematical and technical background has been elaborated in detail e.g. within the context of inverse filtering and particularly concerning the Wiener filter.

In the field of digital image processing, the method of convolution employing the Fourier transform is common use for the filtering of images. Such a filter represents a point spread function (psf) within the frequency domain as a "window function", which is in fact the corresponding MTF. In this context it is important, that apodization functions, which drop to 0 above a certain cut-off frequency, can usefully serve as window functions.

The Hanning function is a commonly used window functions (H) ("raised cosine window") which, used as filter, by complete suppression of spatial frequencies above a certain cut-off frequency results in a smoothening effect but at the same time due to its uniform shape causes relatively small artifacts in the filtered image, such as overshoots at edges. A Hanning function with variable width and a freely determinable frequency limit ω can be defined as follows:

$$H_\omega(v) = 0.5 + 0.5 \cdot \cos(\pi v/\omega) |v| \leq \pi \quad (12a)$$

$$H_\omega(v) = 0 |v| > \pi \quad (12b)$$

Such a Hanning function or a similar apodisation function is suitable for use as an MTF of a virtual imaging system.

Accordingly as an example, using a Hanning function $H_\omega$, a normalized Transconvolution can be defined as follows:

$$F(img) \cdot F(psf^{-1}) \cdot H_\omega = F(img_n) \quad (13)$$

$$F(npsf_\omega) = F(psf^{-1}) \cdot H_\omega \quad (14)$$

$$img \otimes psf^{-1} \otimes F^{-1}(H_\omega) = img_n \quad (15)$$

Here img constitutes the image, which was acquired by the respective imaging system with the point spread function psf.

The function $npsf_\omega$ is the normalized transconvolution function as determined for the respective system based on the respective point spread function and $img_n$ is the resulting normalized image as it would have been acquired by a standardized virtual tomograph.

If the parameter ω is chosen not too high, that is within the limits set by the spatial cut-off frequencies of the participating imaging systems, a numerical calculation is possible in every case.

Interpolation of Non Stationary Point Spread Functions

In case of tomographs or other complex imaging systems, the point spread function is non stationary i.e. position dependent. The calculation of the convolutions becomes thereby more complicated, but can be readily carried out numerically and accordant to the specified method.

Optionally, the method can be adapted to spatially varying point spread functions by suitable interpolation or also possibly by piecewise calculation.

Application of the Virtual Tomograph in Multi-Centre PET Studies

After establishing a suitable study protocol the virtual scanner can be used in the context of quantitative studies as follows:

Phantom measurements are carried out on the participating PET systems—not necessarily at the beginning of the study—under conditions accordingly to the study protocol.

The measurements each self are linearly reconstructed in the manner described and the corresponding PSFs of the participating PET systems are determined.

If the different PSFs of the participating systems are available, it is possible to determine a suitable spatial cut-off frequency ω and to chose a corresponding standardized PSF for the virtual scanner, e.g. in the form of the function $F^{-1}(H_\omega)$ as described in equation (15).

Subsequently, the above described Transconvolution function $npsf_a$, can be determined for each of the participating PET systems.

During the multi-centre study for each measurement and in addition to the usual iterative reconstruction of an image data set optimized for optimal imaging, a second linear reconstruction is calculated and subjected to convolution with the Transconvolution function as determined for the respective tomograph.

The resulting quantitative and normalized second image data set represents a measurement, as it would have been acquired by the virtual tomograph. Both sets of image data can be handled in parallel, visualized, evaluated and stored within the normal procedures. Visual assessment is carried out on the iteratively reconstructed and for imaging optimized image data sets, quantitative analysis of whatever kind are carried out on the bases of said normalized image data sets.

The results of those quantitative analyses are then comparable even for measurements by different systems.

LITERATURE

[BENE01] Benedetto J. Modern sampling theory: mathematics and applications. Birhäuser Boston 2001, ISBN 0-8176-4023-1

[BOEL03] Boellaard R, Krak N C, Hoekstra O S, Lammertsma A A. Effects of noise, image resolution, and ROI definition on the accuracy of standard uptake values: a simulation study. *J Nucl Med.* 2004; 45:1519-1527.

[BOEL09] Boellaard R. Standards for PET image acquisition and quantitative data analysis. *J Nucl Med.* 2009; 50(suppl 2):11S-20S

[BOEL09b] Boellaard R, et al. FDG PET and PET/CT: EANM procedure guidelines for tumour PET imaging: version 1.0, Eur J Nucl Med Mol Imaging, 2009, November

[CHER06] Cherry S R. The 2006 Henry N. Wagner Lecture: Of Mice and Men (and Positrons)—Advances in PET Imaging Technology. J Nucl Med 47: 1735-1745.

[DAUB02] Daube-Witherspoon M E et al. PET Performance Measurements Using the NEMA NU 2-2001 Standard. J Nucl Med 2002; 43:1398-1409

[DELBE2006] Delbeke D, Coleman R E, Guiberteau M J, et al. Procedure guideline for tumor imaging with $^{18}$F-FDG PET/CT 1.0. *J Nucl Med.* 2006; 47:885-895

[ERSO07] Ersoy O K. Diffraction, Fourier Optics and Imaging. Wiley 2007, ISBN 978-0-471-23816-4

[GEWO02] Geworski L, Knoop B O et al. Multicenter comparison of calibration and cross calibration of PET scanners. *J Nucl Med.* 2002; 43:635-639

[GOOD96] Goodman J. Introduction to Fourier Optics. McGraw Hill, 1996, ISBN

[HERR06] Herraiz J L et al. Optimal and Robust PET Data Sinogram Restoration Based on the Response of the System. IEEE 2006 Nuclear Science Symposium Conference Record p. 3404-3407

[HERR07] Herraiz J L et al. Noise and physical limits to maximum resolution of PET images. Nuclear Instruments and Methods in Physics Research A 580 (2007) p. 934-937

[KEYE95] Keyes J W. SUV: Standard Uptake or Silly Useless Value?. *J Nucl Med.* 1995; 36:1836-1839.

[OLDE74] Oldendorf W H. Expression of Tissue Isotope Distribution. J Nucl Med 15: 725-a-726-a.

[SCHE09] Scheuermann J S. Qualification of PET Scanners for Use in Multicenter Cancer Clinical Trials: The American College of Radiology Imaging Network Experience. J Nucl Med 2009 50: 1187-1193.

[SHYA08] Shyam S M et al. A recovery coefficient method for partial volume correction of PET images. Ann Nucl Med (2009) 23:341-348

[SORE07] Soret M et al. Partial-Volume Effect in PET Tumour Imaging. *J Nucl Med.* 2007; 48:932-945

[STRA91] Strauss L G, Conti P S. The Applications of PET in Clinical Oncology. J Nucl Med 1991:32: 623-648.

[TARA03] Tarantola G et al. PET Instrumentation and Reconstruction Algorithms in Whole-Body Applications. J Nucl Med 44: 756-769.

[TOWN08] Townsend D W. Dual-Modality Imaging: Combining Anatomy and Function. *J Nucl Med.* 2008; 49:938-955

[WEST06] Westerterp M et. al., Quantification of FDG PET studies using standardised uptake values in multi-centre trials: effects of image reconstruction, resolution and ROI definition parameters. *Eur J Nucl Med Mol Imaging.* 2007 March; 34(3):392-404. Epub 2006 Oct. 11.

[WOOD75] Woodard H Q et al. Expression of Tissue Isotope Distribution. J Nucl Med 16: 958-b-959-b.

The invention claimed is:

1. A method for standardized and comparable determination of normalized quantitative measurements based on images or image data acquired by different imaging systems, comprising the steps of:
   determining for each of said imaging systems acquisition parameters to be used to acquire said images or image data such that within the capabilities of said imaging system a substantial linear image acquisition is performed;
   determining for each of said imaging systems using said acquisition parameters a stationary or non-stationary point spread function (psf), which describes imaging properties of the respective imaging system;
   defining a stationary or non-stationary point spread function (npsf), which describes imaging properties of a virtual normalized imaging system;
   calculating using transconvolution normalized images or image data (n) starting from images or image data (d) acquired by said imaging systems;
   where said transconvolution is represented as a convolution of the respective acquired images or image data (d) with the result of a convolution of the inverse of said point spread function of the respective imaging system ($psf^{-1}$) with said defined stationary or non-stationary point spread function (npsf) of the virtual normalized imaging system:

$$d \otimes psf^{-1} \otimes npsf = n$$

determining said normalized quantitative measurement values for said acquired images or image data by using a respective set of said calculated normalized images or image data.

2. The method according to claim 1, wherein the image data is one of two-dimensional and represent a measurement in two spatial dimensions, or that the image data are three-dimensional and represent a measurement in three spatial dimensions.

3. The method according to claim 1, wherein the image data comprise one or more additional non-spatial dimensions and said method is carried out only with respect to the spatial dimensions.

4. The method according to claim 1, wherein said measurement of a stationary or non-stationary point spread function (psf), which describes the imaging properties of the respective system, involves the use of a phantom.

5. The method according to claim 4, wherein said phantom contains solid state radiation sources of defined size, shape and activity, and can be used repeatedly for said measurement of the stationary or non-stationary point spread function.

6. The method according to claim 5, wherein the determination of the stationary or non-stationary point spread function (psf), which describes the imaging properties of the respective system, comprises a numerical interpolation or extrapolation of the non-stationary transfer function in accordance with known properties of the respective tomographic system in addition to said measurements using said phantom.

7. The method according to claim 1, wherein said imaging systems are tomographic systems and said image data sets are sinograms.

8. The method according to claim 7, wherein said tomographic systems are emission tomographic systems and configured to perform attenuation correction.

9. The method according to claim 8, wherein said emission tomographic systems are Positron Emission Tomography/Computed Tomography (PET/CT) or Single-Photon Emission Computed Tomography/Computed Tomography (SPECT/CT) systems.

10. The method according to claim 3, wherein said imaging systems are tomographic systems and said image data sets are sinograms.

11. The method according to claim 10, wherein said tomographic systems are emission tomographic systems and configured to perform attenuation correction.

12. The method according to claim 11, wherein said emission tomographic systems are Positron Emission Tomography/Computed Tomography (PET/CT) or Single-Photon Emission Computed Tomography/Computed Tomography (SPECT/CT) systems.

13. The method according to claim 1, wherein said imaging systems are tomographic systems and said image data sets are reconstructed images.

14. The method according to claim 13, wherein said tomographic systems are emission tomographic systems and configured to perform attenuation correction.

15. The method according to claim 14, wherein said emission tomographic systems are Positron Emission Tomography/Computed Tomography (PET/CT) or Single-Photon Emission Computed Tomography I Computed Tomography (SPECT/CT) systems.

16. The method according to claim 3, wherein said imaging systems are tomographic systems and said image data sets are reconstructed images.

17. The method according to claim 16, wherein said tomographic systems are emission tomographic systems and configured to perform attenuation correction.

18. The method according to claim 17, wherein said emission tomographic systems are Positron Emission Tomography/Computed Tomography (PET/CT) or Single-Photon Emission Computed Tomography/Computed Tomography (SPECT/CT) systems.

* * * * *